Jan. 29, 1974 G. H. MACK ET AL Plant Pat. 3,460
CHRYSANTHEMUM PLANT
Filed May 15, 1972
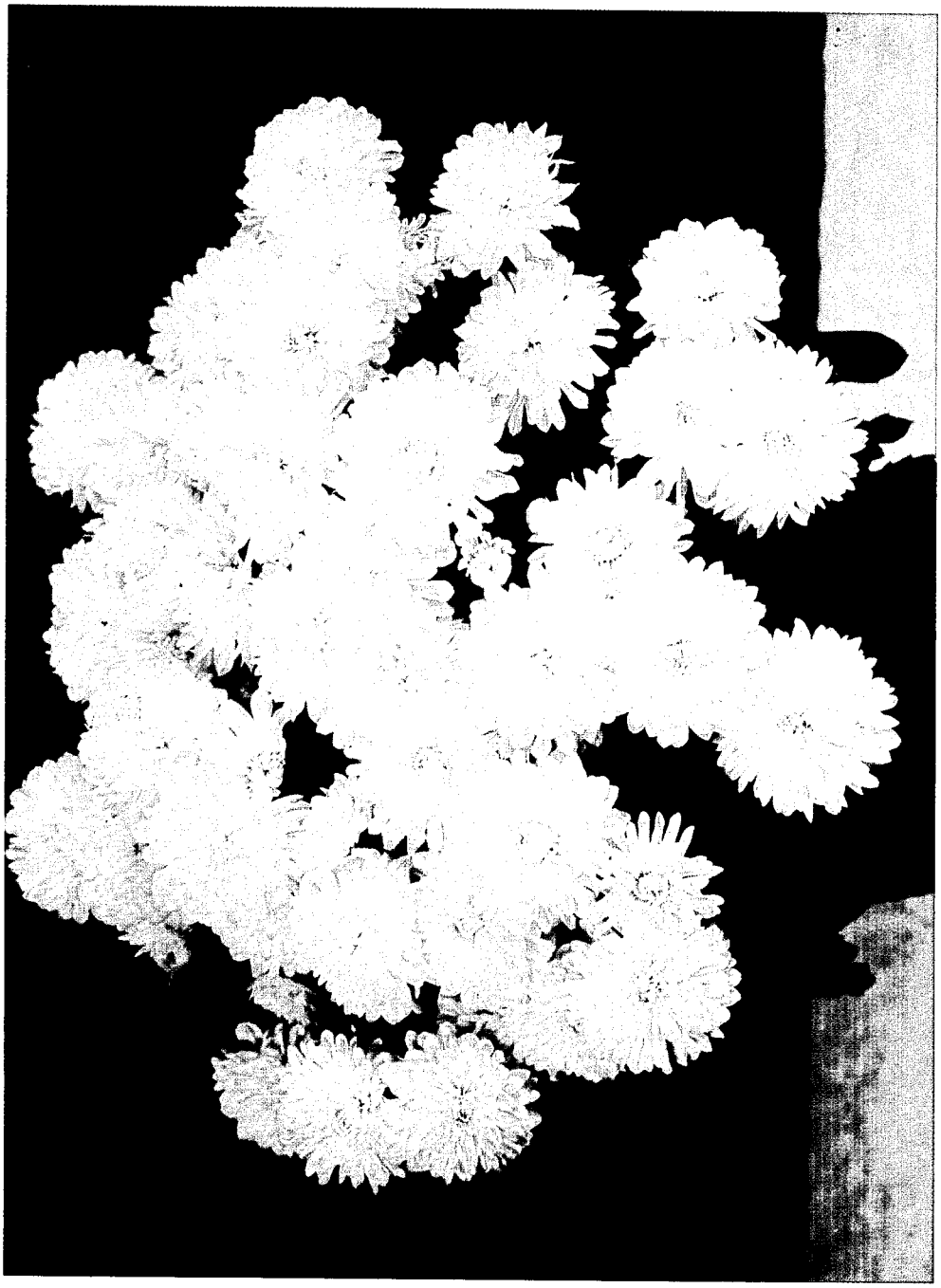

United States Patent Office

Plant Pat. 3,460

Patented Jan. 29, 1974

3,460

CHRYSANTHEMUM PLANT

Grace H. Mack, 108 Wahackne Road, New Canaan, Conn. 06840, and Walter H. Jessel, Jr., Doylestown, and William E. Duffett, Akron, Ohio; said Jessel and said Duffett, assignors to said Mack

Filed May 15, 1972, Ser. No. 253,638

Int. Cl. A01h *5/00*

U.S. Cl. Plt.—75 1 Claim

The present invention comprises a new and distinct cultivar of chrysanthemum plant which is a seedling of #122–62 × Lemon Lace. Both parents are unpatented and identified for breeding purposes in this manner.

The new chrysanthemum cultivar is a garden variety and similar in many respects to the garden variety Yellow Butterscotch, having the same characteristics of:

(1) A similar recommended period of flowering in spring and fall.

(2) Approximately the same flowering response for spring flowerings.

(3) Foilage which is generally similar in size and color, although the leaf edges are more moderately indented and serrated, and the stipules are more prominent in the new cultivar.

The new cultivar is distinguished from Yellow Butterscotch by the following characteristics when grown under comparable conditions:

(1) Approximately ¼ inch smaller flowers.

(2) Several days earlier response than Yellow Butterscotch in a fall natural season flowering in the garden.

(3) Does not reflex its flower form as Yellow Butterscotch.

(4) A plant habit approximately five inches shorter when grown from an outdoor natural season flowering, planted in mid-June and given a single pinch.

(5) Approximately nine inches more spread when grown from an outdoor natural season flowering, planted in mid-June and given a single pinch.

(6) Approximately three to four more breaks per plant when grown from an outdoor, natural season flowering, planted in mid-June and given a single pinch.

(7) A darker yellow flower color.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 7 weeks, and the following detailed description is based on observations made of the new cultivar at and in a greenhouse in Barberton, Ohio. The response time, blooming period, color, and total vigor may vary significantly with varying environmental conditions such as temperature, daylength, and light intensity. Suggested flowering in the northern and western United States is from April through May and September through October; and Florida, January through February.

The accompanying drawing comprises a color photograph of the new cultivar and shows the unique characteristics thereof, with the color being as nearly true as possible with color illustrations of this type.

In the description which follows, color references are made to the Munsell Color Book, 1963 edition, and comparisons are made with the cultivar Yellow Butterscotch. Where only a single value or description appears for the parent cultivar, the same value or description applies to the comparison cultivar.

Botanical classification: *Chrysanthemum morifolium*

| | Classic | Yellow Butterscotch |
|---|---|---|
| Bloom: | | |
| Size | 3″ | 3¼″. |
| Fully expanded | 3½″ | 3¾″. |
| Borne | Clusters on elongated pedicels | |
| Stems | Strong | |
| Form | Decorative | |
| Permanence | 14 days | 10 to 14 days. |
| Color: | | |
| Center of flower | Dark yellow, 6.25Y8/12 | Yellow green, 10Y8.5/10. |
| Base of petals | Green, 2.5GY7/8 | Yellow green, 10Y8/10. |
| Inside of petals | Dark yellow, 6.25Y8/12 to light yellow, 10Y9/6 | Yellow, 7.5Y8.5/12 to light yellow, 7.5Y9/10. |
| Reverse of petals | Light yellow, 10Y9/6 to 10Y9/4 | Light yellow, 7.5Y9/10. |
| Tonality from a distance | Light yellow | Light yellow. |
| Discoloration | Light yellow, 10Y9/6 | Light yellow, 7.5Y9/10. |
| Petals: | | |
| Texture | Smooth | Smooth. |
| Appearance and form | Open at base, broadening quickly to multi-ridged shallow keel, tapering to a blunt point. | Open at base, broadening to a shallow 2-ridged keel, tapering to a reflexed sharp point. |
| Arrangement | Composite, whorled on a single receptacle | |
| Persistence | Resist shatter | Prone to shatter. |
| Fragrance | Typical chrysanthemum | |
| Reproductive organs: | | |
| Stamen, anthers | 0–25 | 0–15. |
| Pollen | None to very scant | None to scant. |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Spreading | |
| Height | Approximately 13″ when grown in an outdoor natural season flowering, planted in mid-June, and given a single pinch. | Approximately 18″ when grown in an outdoor natural season flowering, planted in mid-June, and given a single pinch. |
| Spread | Approximately 24″ when grown in an outdoor natural season flowering, planted in mid-June, and given a single pinch. | Approximately 15″ when grown in an outdoor natural season flowering, planted in mid-June, and given a single pinch. |
| Foliage: | | |
| Top side | Dark green, 7.5GY3/4 | |
| Size | 4″ long, 3½″ wide | 4¼″ long, 3½″ wide. |
| Quantity | Numerous | |
| Shape | Spatulate lobed | |
| Texture | Smooth | |
| Ribs and veins | Moderately prominent | Prominent. |
| Edge | Moderately indented | Deeply indented. |
| Serration | Moderate | Coarse. |
| Under side | Light green, 7.5GY5/4 | |
| Stipules | Very prominent | Rudimentary. |

We claim:

1. A new and distinct cultivar of chrysanthemum characterized particularly as to its uniqueness when compared to the cultivar Yellow Butterscotch by its approximately ¼ inch smaller flower; its several days earlier response than Yellow Butterscotch in fall natural season flowering in the garden; its habit of not reflexing its flower form; its plant habit which is approximately five inches shorter, nine inches more spread and three to four more breaks per plant when grown from an outdoor natural season flowering, planted in mid-June and given a single pinch, and by its darker flower color.

No references cited.

ROBERT E. BAGWILL, Primary Examiner